United States Patent [19]
Goldstein et al.

[11] Patent Number: 4,923,964
[45] Date of Patent: May 8, 1990

[54] HUMAN SPLENIN

[75] Inventors: Gideon Goldstein, Short Hills; Tapan Audhya, Bridgewater, both of N.J.

[73] Assignee: Ortho Pharmaceutical Corporation, Raritan, N.J.

[21] Appl. No.: 53,186

[22] Filed: May 22, 1987

[51] Int. Cl.⁵ .................. A61K 37/02; C07C 103/52
[52] U.S. Cl. ................................... 530/324; 530/301; 530/330; 514/12; 514/17; 514/21; 424/88
[58] Field of Search ................. 530/324, 330, 301; 514/17, 12, 121; 424/88

[56] References Cited

U.S. PATENT DOCUMENTS 4,190,646  2/1980  Goldstein et al. .............. 530/325

OTHER PUBLICATIONS

Audhya et al., "Complete Amino Acid Sequences of Bovine Thymopoietins I, II, and III: Closely Homologous Polypeptides", Biochemistry, vol. 20, pp. 6195–6200, 1981.

Audhya et al., "Contrasting Biological Activities of Thymopoietin and Splenin, Two Closely Related Polypeptide Products of Thymus and Spleen", Proc. Natl. Acad. Sci. USA, vol. 81, pp. 2847–2849, 1984.

*Primary Examiner*—Lester L. Lee
*Assistant Examiner*—Abdel A. Mohamed
*Attorney, Agent, or Firm*—Ortho Pharmaceutical Corporation

[57] ABSTRACT

The present invention is directed to the protein human splenin (hsP), substantially free of material associated with the protein in its natural environment in the human spleen. In particular, the present invention relates to such isolated or synthesized human splenin having the amino acid residue sequence:

-GLY-LEU-PRO-LYS-GLU-VAL-PRO-ALA-VAL-LEU-THR-LYS-GLN-LYS -LEU-LYS-SER-GLU-LEU-VAL-ALA-ASN-ASN-VAL-THR-LEU-PRO-ALA -GLY-GLU-MET-ARG-LYS-ALA-VAL-TYR-VAL-GLU-LEU-TYR-LEU-GLY -SER-LEU-THR-ALA-GLU-HIS-.

Additionally, the present invention relates to a therapeutic composition of matter comprising a therapeutically effective amount of the hsP having the above sequence and a pharmaceutically acceptable carrier.

6 Claims, 4 Drawing Sheets

FIG-5

|     | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|-----|---|---|---|---|---|---|---|---|---|----|----|----|----|----|----|----|----|----|----|----|----|----|----|----|----|
| hSP | GLY | LEU | PRO | LYS | GLU | VAL | PRO | ALA | VAL | LEU | THR | LYS | GLN | LYS | LEU | LYS | SER | GLU | LEU | VAL | ALA | ASN | ASN | VAL | THR |
| hTP | GLY | LEU | PRO | LYS | GLU | VAL | PRO | ALA | VAL | LEU | THR | LYS | GLN | LYS | LEU | LYS | SER | GLU | LEU | VAL | ALA | ASN | GLY | VAL | THR |
| bTP | PRO | GLU | PHE | LEU | GLU | ASP | PRO | SER | VAL | LEU | THR | LYS | GLU | LYS | LEU | LYS | SER | GLU | LEU | VAL | ALA | ASN | ASN | VAL | THR |
| bSP | PRO | GLU | PHE | LEU | GLU | ASP | PRO | SER | VAL | LEU | THR | LYS | GLU | LYS | LEU | LYS | SER | GLU | LEU | VAL | ALA | ASN | ASN | VAL | THR |

|     | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 |
|-----|----|----|----|----|----|----|----|----|----|----|----|----|----|----|----|----|----|----|----|----|----|----|----|----|
| hSP | LEU | PRO | ALA | GLY | GLU | MET | ARG | LYS | ALA | VAL | TYR | VAL | GLU | LEU | TYR | LEU | GLN | SER | LEU | THR | ALA | GLU | HIS |  |
| hTP | LEU | PRO | ALA | GLY | GLU | MET | ARG | LYS | ASP | VAL | TYR | VAL | GLU | LEU | TYR | LEU | GLN | HIS | LEU | THR | ALA | LEU | HIS |  |
| bTP | LEU | PRO | ALA | GLY | GLU | GLN | ARG | LYS | ASP | VAL | TYR | VAL | GLU | LEU | TYR | LEU | GLN | SER | LEU | THR | ALA | LEU | LYS | ARG |
| bSP | LEU | PRO | ALA | GLY | GLU | GLN | ARG | LYS | GLU | VAL | TYR | VAL | GLU | LEU | TYR | LEU | GLN | HIS | LEU | THR | ALA | LEU | LYS | ARG |

HUMAN SPLENIN

BACKGROUND OF THE INVENTION

1. Field of the Invention

This invention relates generally to newly isolated proteins and more particularly to proteins either isolated in purified form from the human spleen or chemically synthesized, and to therapeutic compositions and methods for employing the same.

2. Description of the Prior Art

Immunomodulatory proteins have been isolated from bovine spleen and thymus, and have been analyzed to determine their respective amino acid residue sequences. Additionally, small peptides have been chemically synthesized which mimic the biological activity of the isolated naturally occurring, proteins and have been further modified to be provided with additional attributes such as resistence to enzymic action. A large body of articles and patents have now been published relating to such proteins and synthesized peptides. In particular, see for example Goldstein, G. (1974) Nature (London) 247, 11–14; Basch, R. S. and Goldstein, G. (1974) Proc. Natl. Acad. Sci. U.S.A. 71, 1474–1478; Scheid, M. P., Goldstein, G. and Boyse, E. A. (1978) J. Exp. Med. 147, 1727–1743; Scheid, M. P., Goldstein, G. and Boyse, E. A. (1975) Science 190, 1211–1213; Ranjes, G. E. Scheid, M. P., Goldstein, G. and Boyse, E. A. (1982) J. Exp. Med. 156, 1057–1064; Vankatasubramanian, K., Andhya, T. and Goldstein, G. (1986) Proc. Natl. Acad. Sci. U.S.A. 83, 3171–3174; Malaise M. G., Harz-Hazelstein, M. T., Reuter, A. M., Vrinds-Geort, Y., Goldstein G., and Franchmint, P. (1986) in Immunoregulatory UCLA Symposium on Molecular and Celular Biology, eds. Goldstein, G., Wigzell, H. and Bach, J. F. (Liss, New York),; Sunshine, G. H., Basch, R. S., Coffey, R. G., Cohen, K. W., Goldstein, G. and Hadden, J. W. (1978) J. Immunol. 120, 1594–1599. See also U.S. Pat. Nos. 4,190,646; 4,261,886; 4,361,673; 4,420,424; 4,629,723 and 4,505,853.

The hormone splenin (SP) as obtained from bovine spleen has been described in Audhya et al. Biochemistry, 20, 6195–6200 (1981). As described therein, bovine splenin (bSP) has been determined to be a 49 amino acid residue peptide having an amino acid residue sequence differing from bovine thymopoietin (bTP) by two amino acid residues at positions 34 and 43. This difference is significant in that the 34 position is believed to lie within the active-site region of the protein and a change therein will affect the receptor specifications and biological activity of the molecule.

While extensive work has been done in connection with bovine SP, to date however, human SP (hSP) has not been isolated from human spleen tissue and, of course, neither has the protein been completely sequenced or synthesized.

SUMMARY OF THE INVENTION

The present invention relates to the protein human splenin, Substantially free of non-human splenin native material i.e., free of such material associated with the protein in its natural environment in the human spleen. In particular, the present invention relates to such isolated or synthesized human splenin having the amino acid residue sequence:
-GLY-LEU-PRO-LYS-GLU-VAL-PRO-ALA-VAL-LEU-THR-LYS-GLN-LYS -LEU-LYS-SER-GLU-LEU-VAL-ALA-ASN-ASN-VAL-THR-LEU-PRO-ALA -GLY-GLU-MET-ARG-LYS-ALA-VAL-TYR-VAL-GLU-LEU-TYR-LEU-GLY -SER-LEU-THR-ALA-GLU-HIS-.

Additionally, the present invention relates to a therapeutic composition of matter comprising a therapeutically effective amount of the hSP having the above sequence and which may include among other ingredients a pharmaceutically acceptable carrier. Specifically, such therapeutically effective amount of polypeptide may be at least about 1–1000 µg/kg of body weight.

In a further aspect of this invention the therapeutic composition described above may be used in the treatment of various conditions related to the reported biological activity of hSP such as for example, in correcting conditions resulting from relative or absolute deficiencies of the thymus or spleen. The composition may be employed to induce certain desirable reactions related to the biological activity of hSP such as to induce the differentiation or maturation of T cells or B cells.

BRIEF DESCRIPTION OF THE DRAWINGS

FIG. 5 illustrates the full sequences of amino acid residues for hSP as contrasted to hTP, bTP, and bSP. The ten species specific residues shared by TP and SP within each species are show with heavy stippling in the human sequences. Within the active site region (32–36), bTP and hTP are identical, but bSP and hSP differ at position 34.

DETAILED DESCRIPTION OF THE INVENTION

Figure 1:
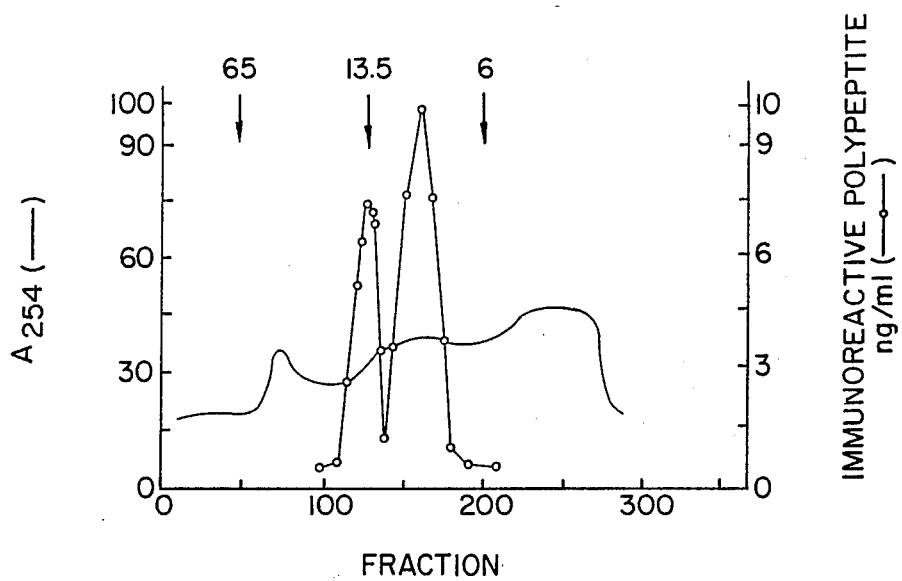
FIG. 1 illustrates, graphically, the result of Sephedex G-75 molecular sieve chromatography of extracts of human spleen with measurement of immunoreactive material by RIA for bTP. The lower molecular weight peaks were further purified to yield hSP.

As used herein the following abbreviations shall apply: SP, splenin; hSP, human SP; bSP, bovine SP; FPLC, fast protein liquid chromatography. Further, throughout this disclosure, the amino acid components of the peptides and certain materials used in their preparation are identified by abbreviations for convenience. These abbreviations are as follows:

| Amino Acid | Abbreviation |
| --- | --- |
| L-alanine | ALA |
| D-alanine | D-ALA |
| L-arginine | ARG |
| D-arginine | D-ARG |
| L-aspartic acid | ASP |
| D-aspartic acid | D-ASP |
| L-glutamic acid | GLU |
| D-glutamic acid | D-GLU |

| Amino Acid | Abbreviation |
|---|---|
| D-glutamine | D-GLN |
| L-histidine | HIS |
| D-histidine | D-HIS |
| L-isoleucine | ILE |
| D-isoleucine | D-ILE |
| L-leucine | LEU |
| D-leucine | D-LEU |
| L-lysine | LYS |
| D-lysine | D-LYS |
| α-methylalanine | AIB |
| L-phenylalanine | PHE |
| D-phenylalanine | D-PHE |
| L-proline | PRO |
| L-tryptophan | TRP |
| D-tryptophan | D-TRP |
| L-valine | VAL |
| D-valine | D-VAL |

In its broadest aspect this invention is concerned with human splenin in a form substantially free of native material, i.e. either isolated from human spleen or synthesized, and to therapeutic compositions employing the same.

ISOLATION AND CHARACTERIZATION OF HUMAN SPLENIN

The scheme for isolation of hSP from human spleen is best illustrated by the Flow Sheet, Scheme 1, below:

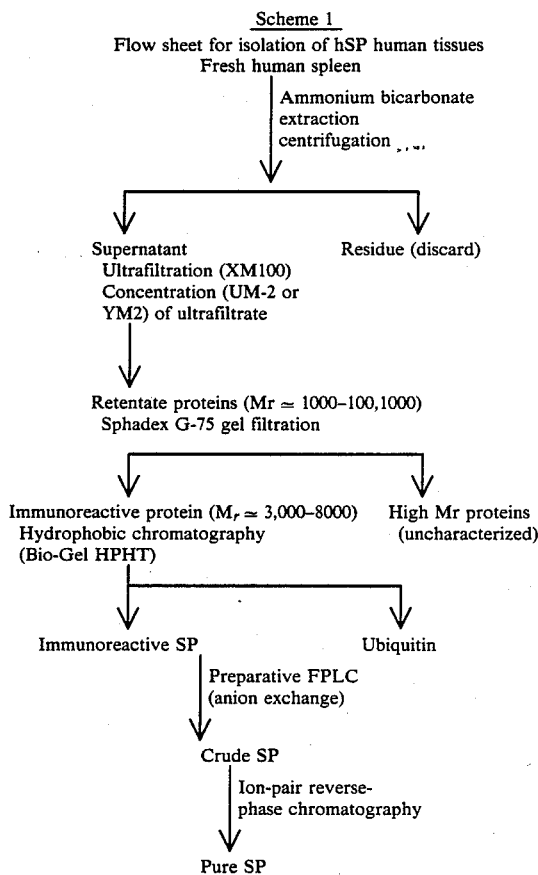

Human spleen from surgical or autopsy specimens were trimmed and stored at −35° C. Separation materials and apparatus were purchased commercially: Sephadex (Pharmacia), hydroxyapatite (Bio-Gel HPHT; Bio-Rad), and preparative large-pore anion-exchange column (2.5×25 cm; DE 500, particle size 40-60 μ) for HPLC (Separation Industries, Metuchen, N.J.).

The purification of hSP was monitored by using a RIA for bTP that was cross-reactive with hSP (Goldstein, G. (1976) J. Immunol. 117, 690-692 and Lisi, P. J., Teipel, J. W., Goldstein, G. & Schiffman, M. (1980) Clin. Chem. Acta 107, 111-119). Briefly, bTP was labeled with $^{125}I$ by the Bolton-Hunter method (Bolton, A. E. & Hunter, W. M. (1973) Biochem. J. 133, 529-539), and the radiolabeled bTP was purified as described (Audhya, T., Talle, M. A. & Goldstein, G. (1984) Arch. Biochem. Biophys. 234, 167-177). Anti-bTP antibody (diluted 1:10,000) was $^{125}I$-labeled bTP (10,000 cpm), in the presence or absence of various peptide fractions in phosphate buffer, were incubated for 8 hr. at 22° C. Separation of bound and free bTP was with 24% polyethylene glycol at room temperature, followed by centrifugation at 2000 rpm for 15 min. The bound bTP was assayed in a LKB γ spectrometer.

A 9000 g batch of human spleen was extracted in ice-cold 100 mM ammonium bicarbonate [25% (net weight) containing 50 ng of 2-mercaptoethanol, 175 μg of phenylmethylsulfonyl fluoride, and 375 μg of EDTA per ml) by homogenization in a Waring Blender (Dynamics, New Hartford, Conn.). After centrifugation at 14,000×g for 10 min. at 4° C., the supernatant was filtered through cheese cloth and stored at 4° C. after addition of 0.1% thimerosal and 0.1% sodium azide. The extract was processed through an Amicon hollow fiber cartridge H10×100, followed by concentration on a Diaflo YM2 membrane in a thin-channel ultrafiltration system.

Scheme 1 (above) summarizes the isolation procedures. The retentate of the UM2 or YM2 filtration was chromatographed on bead-type Sephadex G-75 (particle size, 40-120 μm) at room temperature on a 5×150 cm column in lyophilized. Two major peaks containing immunoreactive material were found. (FIG. 1). The lower molecular weight peak ($M_r$ 5000-8000) was processed further by hydroxyapatite column chromatography using Bio-Gel HPHT (2.5×60 cm column; 5 mM sodium phosphate buffer, pH 6.8), the sample being applied in the same buffer. Elution was with 30 ml of the same buffer and then with 35 ml of 50 phosphate buffer Immunoreactive fractions were pooled, concentrated on an Amicon Diaflo UM2 membrane, desalted on an 0.6×30 cm Sephadex G-25 (fine) column in 10 mm ammonium bicarbonate (pH 8.0), and lyophilized.

After hydroxyapatite column chromatography, fast protein liquid chromatograph (FPLC) was performed with a Mono Q HR 5/5 column (Pharmacia). Elution was with 20 mM monoethanolamine (pH 9.5) and a linear gradient finishing with 0.3 M NaCl in the same solvent. The eluted fractions were partially evaporated, lyophilized, and reconstituted in 500 μl of ammonium bicarbonate. Volumes of 10 μl were tested in duplicate by RIA, and the immunoreactive fractions were pooled and lyophilized.

Yields from the purification steps are seen in Table 1.

TABLE 1
Summary of purification of hSP

| Purification Step | Total protein, mg | Immunoreactive protein mg | Immunoreactive protein % | Fold purifcat. | Rec. % |
|---|---|---|---|---|---|
| Ultrafilt. protein | 230.9 | 134.7 | 0.05 | 1 | 100 |
| Gel filt. of G-75 | 305.8 | 97.3 | 3.2 | 650 | 72* |
| Hydroxyap. Chromat. | 148.5 | 66.3 | 45 | 900 | 49 |
| Preparative FPLC | 22.5 | 17.4 | 77 | 1540 | 12.9 |
| Reverse-phase Chromat. | 6.8 | 6.1 | 90 | 1800 | 4.5 |

*Lower molecular weight peak.

Amino acid analysis was performed with a Liquimat III amino acid analyzer following acid hydrolyses in 5.7 M HCl containing 0.5-2 mercaptoethanol for 22 hr at 100° C. (Speckman, D. H., Stein, W. H. & Moore, S. (1958) Anal. Chem. 30, 1190-1206).

Maleated hSP was prepared by adding maleic anhydride in 1,4-dioxane (100 μl) was added at a 20-fold excess over the free amino groups of the polypeptides (500 μg), which were dissolved in 100 mM sodium borate (pH 9.3). Maleic anhydride was added stepwise over a 4-hr period,; H 9.3 being maintained with 6 M NaOH. The maleated protein was then desalted on Bio-Gel P-2 in 100 mM NH$_4$HCO$_3$ (pH8.2) and lyophilized.

Tryptic digestions of maleated hSP were carried out in 0.2 M N-ethylmorpholine acetate buffer (pH 8.1) at 37° C. for 6 hr. Bovine pancreatic trypsin (diphenylcarbamyl chloride-treated; 8400 Nα-benzoyl-L-arginine ethyl ester units per mg of protein, Sigma type XI) was added to a final enzyme/substrate ratio of 1:100 (on a weight basis). The pH was maintained at 8.5 during the digestion and then lowered to a 2.0 by addition of 10 mM HCl to terminate the reaction. The mixture was then lyophilized.

hSP (200 pmol) were cleaved with CNBr in 150 μl of 70% formic acid for 23 hr at room temperature in the dark; a 200-fold molar excess of CNBr over the methionine content in the sample was used. The volume was then reduced to 60 μl under N$_2$ and applied directly on to the glass filter of the gas-phase sequencer (Hunkapiller, M. W., Hewick, R. M., Dryer, W. J. & Hood, L. (1983) Methods Enzymol. 91, 399-413).

The trypsin digested and CNBr-cleaved peptides were purified in the following manner. The tryptic peptides were dissolved in 0.1% orthophosphoric acid (pH 2.2) and were centrifuged at 15,600×g for 5 min; the supernatant was applied to the C$_{18}$ reverse-phase column [Vydac 218TP54, 46 mm×25 cm, 5-μm particle size,) The Separation Group, Hesperia, Calif.)] for HPLC (LDC gradient module with spectromonitor II and CI-10 computing integrator attached to a LKB Redirac fraction collector 2112). A linear elution gradient was used starting with 0.1% phosphoric acid and finishing with 80% acetonitrile. High purity-grade acetonitrile was obtained from Burdick and Jackson (Muskegon, Miss.) and distilled in glass. Phosphoric acid (1%) was filtered through a Millipore type HA 0.45-μm filter (Millipore). All solvents were degassed for 20 min under vacuum with stirring.

Automated sequence analyses on intact hSP, and tryptic and cyanogen bromide fragments of hSP were performed by gas-phase sequencing that used a model 470A applied biosystems gas-phase sequencer with Polybrene as carrier and a standard single-coupling sing cleavage program. The resulting phenylthiohydantoin-derivatized amino acids were identified by HPLC with a 1084B Hewlett Packard high-pressure liquid chromatograph (Schlesinger, D. H. (1983) Methods Enzymol. 91, 494-502).

C-terminal analysis of hSP (150 μg each) was performed with yeast carboxypeptidase Y (2 nmol) dissolved in 100 mM sodium acetate (pH 6.0) at 37° C. At various periods, aliquots were removed from the digest and added to tubes containing μl of glacial acetic acid, and the mixture was then lyophilized. The sample was dissolved in 0.2 M sodium citrate (pH 2.2) and applied to the amino acid analyzer. Enzyme and peptide blanks were also run.

As a result of the above methods, approximately 9 kg of freshly frozen spleen yielded 6 mg of homogenous protein (recovery 4.5%; Table 1). Analytical disc gel electrophoresis at pH 8.9 and 4.3 gave a single sharp band with an isoelectric point of 6±0.15.

The amino acid composition is shown in Table 2.

TABLE 2
Amino acid compositin of hSP (molar ratios)

| Amino Acids | Found | Mean +SD* |
|---|---|---|
| Cysteic acid | 0 | ND |
| Aspartic acid | 2 | 1.78 ±0.13 |
| Threonine | 3 | 2.86 ±0.18 |
| Serine | 2 | 1.84 ±0.13 |
| Glutamic acid | 7 | 7.36 ±0.42 |
| Proline | 3 | 2.56 ±0.18 |
| Glycine | 2 | 2.22 ±0.14 |
| Alanine | 5 | 4.84 ±0.17 |
| Valine | 6 | 5.62 ±0.27 |
| Methionine | 1 | 0.89 ±0.14 |
| Isoleucine | 0 | 0.21 ±0.12 |
| Leucine | 8 | 8.41 ±0.41 |
| Tyrosine | 2 | 1.69 ±0.19 |
| Phenylalanine | 0 | 0.22 ±0.10 |
| Lysine | 5 | 5.36 ±0.34 |
| Histidine | 1 | 0.96 ±0.13 |
| Arginine | 1 | 1.16 ±0.12 |

ND, not detected.
*Average of two determinations (24 and 76 hr). Serine was increased by 10% and threonine by 5% to compensate for destruction by acid. Hydrolysis was performed with constant-boiling HCl at 110° C. in vacuo.

Figure 2:
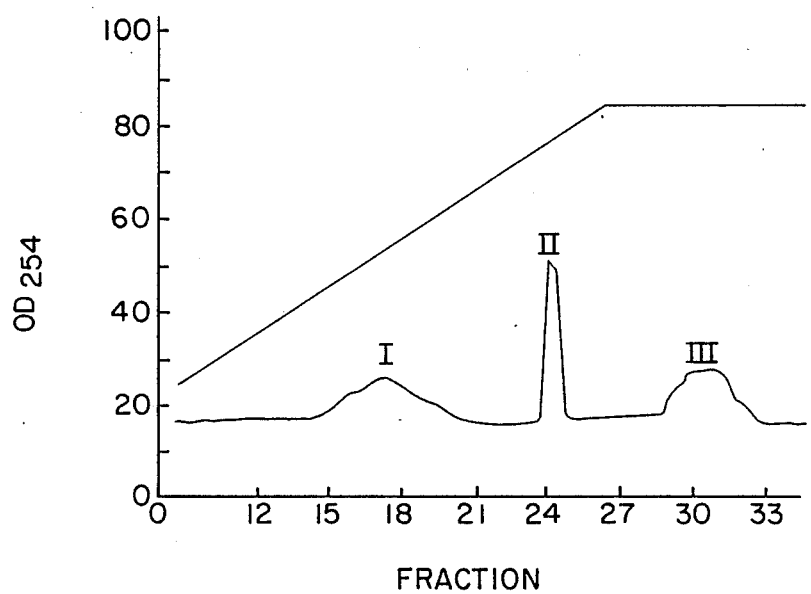
FIG. 2 illustrates graphically the result of separation of CNBr digest of hSP dissolved in 0.1% orthophosphoric acid on a $C_{18}$ reverse-phase column (Vydec 218TP54, 46 mm×25 cm) at a flow rate of 2 ml/min. The peaks are designated I, II, and III. The gradient line represents the presence of organic solvent.

CNBr cleavage of the hSP produced three peaks (FIG. 2). The amino acid sequence and results for each are summarized in Table 3.

Figure 4:
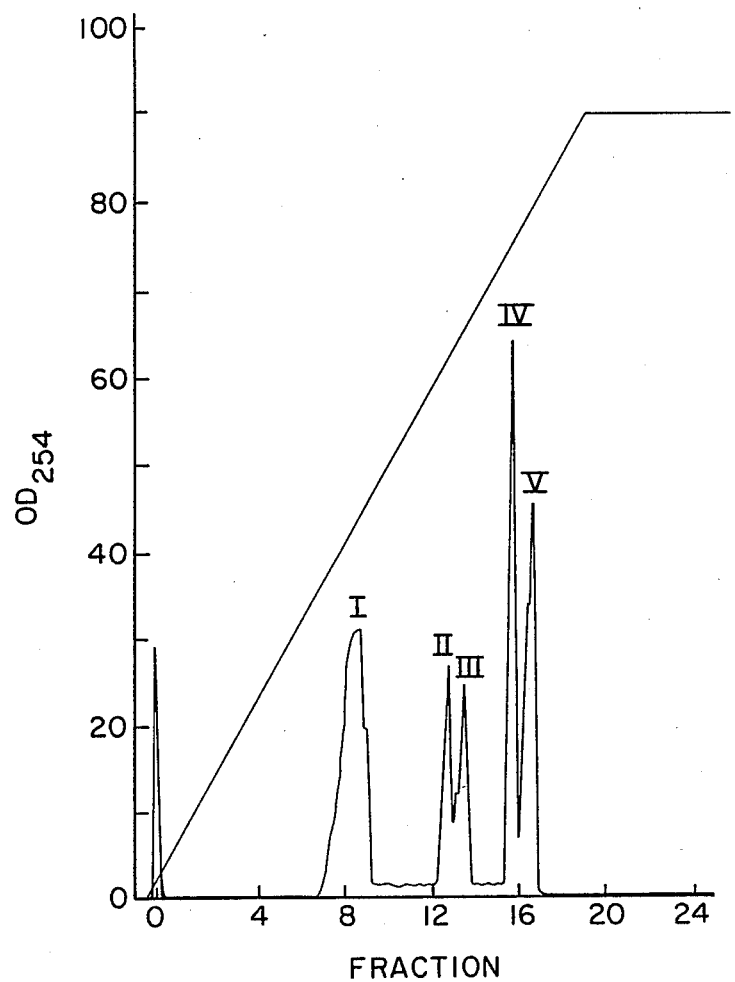
FIG. 4 illustrates the elution profile of the tryptic digest of maleated hSP on Mono Q HR 5/5 (Pharmacia) column used in HPLC system. Five major peptide containing peaks were detected by UV absorption at 254 nm. These are designated I-V.

Tryptic Digestion of Maleated hSF and Separation of Fragments. Maleated tryptic digestion of hSP produced five distinct peaks on HPLC (FIG. 4). The sequence regions of peptide in each peak are summarized in Table 3.

TABLE 3
Methods of sequence determination for the various regions of hSP.

| Method of Sequencing | Residues Identified |
|---|---|
| N-terminal degradation | |
| Native SP CNBr cleavage | 1-34 |
| Peak I | 1-16 |
| Peak II | 32-39 |
| Tryptic digest of maleated SP | |
| Peak I | 1-15 |
| Peak II | 8-20 |
| Peak III | 37-47 |
| Peak IV | No sequence obtained |
| Peak V | 18-30 |
| C-terminal carboxypeptidase method | 45-48 |

Figure 3:
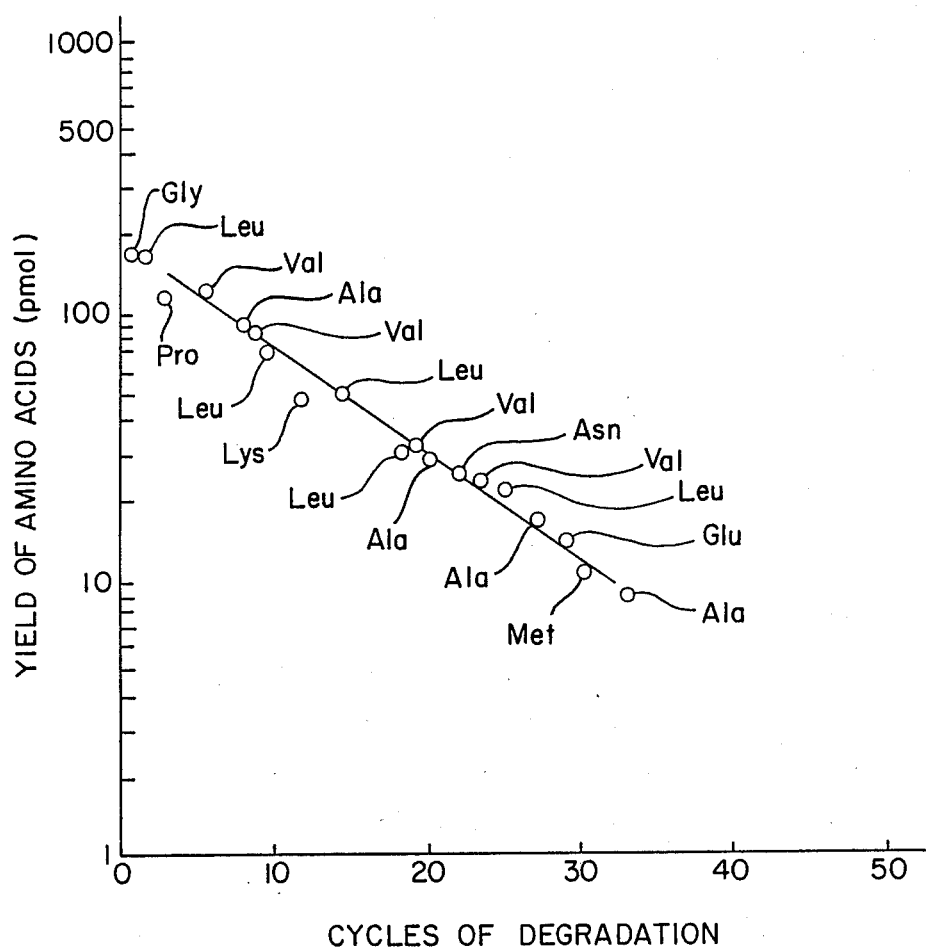
FIG. 3 illustrates graphically the repetitive yields of phenylthiohydantoin-derivatized amino acids during automated Edman degradation of hSP through 46 cycles.

The structural determination of hSP was carried out as follows. hSP (110 pmol) was subjected to automated gas-phase sequence analysis by Edman degradation, and continuous identifications were made through the N- terminal 34 residues. The average yield per cycle was 90.2%, and the measured recoveries of selected residues are shown in FIG. 3. The C-terminal sequence (Table 4) of the intact protein was determined with carboxypeptidase y giving time-dependent release of amino acids. The C-terminal sequence of -Ala-Glu-His-COOH- provided a two-amino acid sequence overlap with the sequence of peak II obtained from a try? tic digest of maleated hSP (FIG. 4). Amino acid compositions of hSP and the fragments obtained from both CNBr cleavage and enzymatic digestion were consistent with the N-terminal sequence determinations and the sequence completion by carboxypeptidase analysis.

TABLE 4

Release of free amino acids with time from the C terminus with carboxypeptidase Y

| Amino acid | Amino acid yield, nmol | | | | | |
|---|---|---|---|---|---|---|
| | 100s | 120s | 150s | 200s | 250s | 300s |
| | hSP | | | | | |
| Ala | — | — | — | 0.32 | — | 0.80 |
| Glu | 0.27 | — | — | 0.80 | — | 0.80 |
| His | 0.91 | — | — | 0.80 | — | 0.90 |

SUMMARY OF ISOLATION AND CHARACTERIZATION OF HSP

Previously, the cross-reactivity of anti-bTP antibodies were used to detect and isolate the closely related polypeptide bSP from bovine spleen (Audhya, T., Schlesinger, D. H. & Goldstein, G. (1981) Bio-chemistry 20, 6195–6200). Similarly, antibodies to bTP proved cross-reactive with hSP, and the bTP RIA was used to monitor the isolation of hSP from extracts of human thymus, and spleen respectively. The isolation involved tissue extraction in aqueous solvent, ultrafiltration for approximate sizing, hydrophobic chromatography, and anion-exchange FPLC. Approximately 50% of the immunoreactive material in the extract was present in a higher molecular weight form that probably represents a biologically inactive Precursor form (Steiner, D. F. & Oyer, P. E. (1967) Proc. Natl. Acad. Sci. USA 57, 473–480). This was separated during molecular sieving on Sephadex G-75.

Splenin yields of 4.5% (1800 fold purification) (Table 4) was comparable to the yields for bSP (Audhya, T., Schlesinger, D. H. & Goldstein, G. (1981) Biochemistry, 20, 6195–6200). Purity of hSP was established by polyacrylamide gel electrophoresis, HPLC, and amino acid sequence.

Residues 1–34 were determined by automated Edman degradation with the gas-phase sequencer, with confirmation of residues 1–16 from a CNBr-cleavage fragment, and extension of sequence 32–39 was determined from the other CNBr-cleavage fragment. This provided independent confirmation of the active-site region of hSP, which is different from that of bSP and from those of both bTP and hTP (see below). The remaining sequence was determined from Edman degradation of fragments produced by tryptic digestion of maleated hSP (residues 1–15, 8–20-18–30, and 37–47) and by time release carboxypeptidase digestion (residues 45–48). Tryptic cleavage of maleated hSP yielded fragments that represented cleavages between residues 7–8 (-Pro-Ala-), 17–18 (-Ser-Glu-), and 36–37 (-Tyr-Val-); there was no cleavage at the protected site 31–32 (-Met-Arg-). We are at a loss to explain these anomalous cleavages other than that they are attributable to contaminating enzymes in the trypsin preparation and not to trypsin itself.

Referring to FIG. 5, hSP and human thymopoietin (hTP) (as disclosed in a copending application Ser. No. 53,286, filed on this same day and incorporated herein by reference) were very similar in amino acid sequence, each being 48-amino acid linear polypeptides differing in only 4 residues, positions 23, 34, 43, and 47. They were also similar to bTP and bSP (bovine spleen), with 10 residues being similar between hTP and hSP but different from the common residues in bTP and bSP at these positions. These comparisons confirm that the amino acid sequences of hTP and hSP were indeed determined and indicate that gene conversion must have occurred during evolution to maintain the parallel sequence evolution of these two polypeptides within each species. Other important gene systems that utilize gene conversion include immunoglobulin(Schreier, P. H., Bothwell, A. L. M., Muller-Hile, B. & Baltimore, D. (1981) Proc. Natl. Acad. Sci. U.S.A. 78, 4495 4499) and the major histocompatibility complex (Steinmetz, M. & Hood, L. (1983) Science 222, 727–733) genes. Maintenance of parallel evolution of regions of TP and SP outside the active-site region (residues 32–36) implies that these C- and N-terminal regions of the molecule must also have an important function, with similar requirements for both TP and SP being maintained within each species.

Residues 32–36 of bTP are known to represent the active site, with the corresponding synthetic TP-(32–36) pentapeptide TP-5 having the biological activities of TP in animals and man (Goldstein. G., Scheid, M. P., Boyse, E. A., Schlesinger, D. H. & Van Wauwe, J. (1979) Science 204, 1309–1310, Audhya, T., Scheid, M. P. & Goldstein, G. (1984) Proc. Natl Acad. Sci. U.S.A. 81, 2847–2849). The present studies establish that the active site of hTP (residues 32–26) is identical with that of bTP, so that synthetic TP-5 (Arg-Lys-Asp-Val-Tyr) also represents the human active site.

bSP differs from bTP by having a glutamic acid reside at position 34, in contrast to aspartic acid at this position in bTP, and this change confers contrasting biological activities on bSP and synthetic splenopentin or SP-5 (Arg-Lys-Glu-Val-Tyr) by comparison with bTP and TP-5. Interestingly, hSP has an alanine at position 34, thus differing from bSP and TP. hSP differs in its biological activity from bSP in that hSP but not bSP induces elevation of intracellular cGMP in MOLT-4, a human T-cell line (B. Baker, G. Viamontes, T. A. and G. G., unpublished data). Therefore, it was predicted that the active site of hSP would have changed from that of bSP, and this is now confirmed directly from the amino acid sequence.

It is contemplated that the peptide of this invention, in addition to being isolated from human spleen may also be produced by the intervention of the hand of man e.g., either recombinantly, using genetic engineering techniques or synthetically, using chemical synthesis. Conveniently, the peptides may be prepared following the solid phase synthetic technique initially described by Merrifield in JACS, 85, 2149–2154 (1963). Such methods are also disclosed in certain of the prior art patents referred to above. Other techniques may be found, for example in M. Bodanszky, et al., Peptide Synthesis, John Wiley & Sons, second edition, 1976, as well as in other reference works known to those skilled in the art. Appropriate protective groups usable in such synthesis and their abbreviations will be found in the above texts, as well as in J. F. W. McOmie, Protective Groups in Organic Chemistry, Plenum Press, New York, 1973. Both of these books are incorporated herein by reference. The common protective groups used herein are t-butyloxycarbonyl (BOC), benzyl (BZL), t-amyloxycarbonyl (AOC), tosyl (TOS), o-bromophenylmethoxycarbonyl (BrZ), 2-6 dichlorobenzyl (BZLCl$_2$), and phenylmethoxycarbony 1 (Z or CBZ).

Because of the immunomodulatory characteristics of the subject peptides, they are therapeutically useful in the treatment of humans and animals, since they have the capability of inducing the differentiation and maturation of T-cells and B-cells which are capable of involvement in the immune response of the body. As a result, the subject peptides are considered to have multiple therapeutic uses.

Primarily, since the compounds have the capability of carrying out certain of the indicated functions of the spleen, they have application in various splenic function and immunity areas. Additionally, the subject peptides are considered useful in assisting the collective immunity of the body, in that they will increase or assist in therapeutic stimulation of cellular immunity and thereby are useful in the treatment of diseases involving chronic infection, such as fungal or mycoplasma infections, tuberculosis, leprosy, acute and chronic and viral infections and the like.

The subject compounds are generally considered to be useful in any area in which cellular immunity is an issue and particularly where there are deficiencies in immunity. Thus, where there is an excess of antibody production due to unbalanced T cells and B cells, the subject peptides can correct this condition by stimulating cell production. Thus, they are expected to be of therapeutic use in certain autoimmune diseases in which damaging antibodies are produced, such as systemic lupus erythematosis, rheumatoid arthritis, or the like.

In their broadest application, the subject compounds are useful for regulating the immune system of a subject, human or animal, in need of such regulation. As used herein, the term "regulate" means that the subject compounds cause the immune system to return from an abnormal, diseased state to a normal, balanced state. While this regulation may well find great application in the correction of immunological deficiencies (e.g., DiGeorge syndrome), it is also applicable to correct conditions of excess immunological activity (e.g., autoimmune diseases). The present invention therefore includes methods for regulating the immune system of a subject in need of such regulation which comprises administering to said subject an immunoregulatorily-effective amount of one of the subject compounds, as well as pharmaceutical compositions for practicing these methods.

The invention also provides a method for treatment of conditions resulting from relative or absolute deficiencies of the spleen of a subject which comprises administering to said subject a therapeutically-effective amount of the hSP. As used herein, the term "therapeutically-effective amount" means an amount which is effective to treat the respective conditions or deficiencies of the spleen. The invention also provides a method for inducing the differentiation and maturation of B-cells and T-cells which comprises administering to the subject an effective inducing amount of the hSP. The invention further provided pharmaceutical compositions for practicing those methods.

To prepare the pharmaceutical compositions of the present invention, the hSP is combined as the active ingredient in intimate admixture with a pharmaceutical carrier according to conventional pharmaceutical compounding techniques. This carrier may take a wide variety of forms depending on the form of preparation desired for administration, e.g., sublingual, rectal, nasal, oral, or parenteral. In preparing the compositions in oral dosage form, any of the usual pharmaceutical media may be employed, such as for example, water, oils, alcohols, flavoring agents, preservatives, coloring agents and the like in the case or oral liquid preparation (e.g., suspensions, elixirs, and solutions) or carriers such as starches, sugars, diluents, granulating agents, lubricants, binders, disintegrating agents, and the like in the case of oral solid preparations (e.g., powders, capsules, and tablets). Controlled release forms may also be used. Because of their ease in administration, tablets and capsules represent the most advantageous oral dosage unit form, in which case solid pharmaceutical carriers are obviously employed. If desired, tablets may be sugar coated or enteric coated by standard techniques.

For parenteral products, the carrier will usually comprise sterile water, although other ingredients to aid solubility or for preservation purposes (for example) may be included. Injectable suspensions may also be prepared, in which case appropriate liquid carriers, suspending agents, and the like may be employed.

The hSP is generally active when administered parenterally in amounts above about 1 μg/kg of body weight and preferably from about 0.1 to about 10 mg/kg body weight. Generally, the same range of dosage amounts may be used in treatment of the diseases or conditions mentioned where immunodeficiency is to be treated. Larger amounts (e.g., about 10–100 mg/kg body weight) are useful for suppressing excess immune activity.

What is claimed is:

1. A protein, splenin, substantially free of other human proteinaceous material, comprising the amino acid sequence as follows:
-GLY-LEU-PRO-LYS-GLU-VAL-PRO-ALA-VAL-LEU-THR-LYS-GLN-LYS-LEU-LYS-SER-GLU-LEU-VAL-ALA-ASN-ASN-VAL-THR-LEU-PRO-ALA-GLY-GLV-MET-ARG-LYS-ALA-VAL-TYR-VAL-GLU-LEU-TYR-LEU-GLN-SER-LEU-THR-ALA-GLU-HIS-, said protein having the ability to induce elevation of intracellular cGMP as measured by an assay with MOLT-4 T-cells.

2. The protein according to claim 1 characterized by the following biophysico-chemical characteristics:
   (a) a molecular sieve chromatographic molecular weight peak of about $M_r$ 5000–8000; and
   (b) an electrophoretic isoelectric point of about 6.0±0.15.

3. A peptide comprising the sequence of amino acid residues ARG-LYS-ALA-VAL-TYR.

4. A pharmaceutical composition comprising a therapeutically effective amount of the protein of claim 1 and a pharmaceutically acceptable carrier.

5. A pharmaceutical composition comprising a therapeutically effective amount of the peptide of claim 3 and a pharmaceutically acceptable carrier.

6. The peptide according to claim 3, further characterized by the ability to induce elevation of intracellular cGMP as measured by an assay with MOLT-4 T-cells.

* * * * *